United States Patent [19]
Zikria et al.

[11] Patent Number: 5,565,187
[45] Date of Patent: Oct. 15, 1996

[54] METHODS FOR STUDYING CAPILLARY CIRCULATION USING FISH FRY AND TADPOLES

[76] Inventors: Bashir Zikria; Suraya Zikria, both of 196 Millbrook Cir., Norwood, N.J. 07640

[21] Appl. No.: 500,137

[22] Filed: Jul. 10, 1995

Related U.S. Application Data

[63] Continuation of Ser. No. 68,772, Jun. 1, 1993, abandoned.

[51] Int. Cl.⁶ ........................................ G01N 33/28
[52] U.S. Cl. .................. 424/9.6; 424/9.1; 424/9.2
[58] Field of Search ............. 424/3, 7.1, 9, 9.1, 424/9.2, 9.6; 119/3

[56] References Cited

U.S. PATENT DOCUMENTS 3,565,041  2/1971  Brooks ........................................ 119/3

OTHER PUBLICATIONS

D E Hinton et al (1989) Mar. Environ. Res. 28:407–410 (Abstract only).
M Romanus et al (1983) Arch Phys Med Rehabil 64:553–555.
VWR Scientific 1989/1990 catalog p. 1498.

*Primary Examiner*—Bruce R. Campbell
*Attorney, Agent, or Firm*—Evelyn M. Sommer

[57] ABSTRACT

A method is provided for studying capillary circulation utilizing intravital microscopy. The method comprises providing an intact living Salmonid or other Teleost alevin with yolk sac attached in a small water filled plastic bag or tube for immobilizing the fish fry. Thereafter there is injected into the yolk sac, a fluorescent dye complex and tracer FITC-DX (MW 150,000 daltons) and the absorption of the injected material into the systemic circulation of said living Salmonid or Teleost alevin tracked by means of fluorescent microscopy. The method can be used for carrying out toxicological pharmacological, physiological, embryological, oncological, pathological, etc. studies.

14 Claims, No Drawings

METHODS FOR STUDYING CAPILLARY CIRCULATION USING FISH FRY AND TADPOLES

This application is a continuation of application Ser. No. 08/068,772, filed Jun. 1, 1993, now abandoned.

This invention relates to a new model for research studies involving capillary circulation by intravital microscopy and for use in clinical test procedures lending themselves to evaluation through intravital microscopic studies of capillary circulation and to test procedures utilizing the new models.

Intravital microscopic studies of capillary circulation have in the past involved primarily frogs (tongue, hindfeet, mesentery), hamsters (cheek pouch), rats (cremasteric muscle and mesentery) and rabbits (ears).

In accordance with this invention, there is now provided a new, convenient, inexpensive and practical model for research of capillary circulation by intravital microscopy as well as methods for carrying out a broad range of biological, toxicological, pharmacological, industrial and environmental toxicological and like procedures.

Thus in addition to the new model, there are also provided procedures using such models for carrying out toxicological, pharmacological, physiological, embryological, oncological and pathological studies. Further the model is ideal for studying the pathology, physiology, pharmacology of inflammation and immunology.

The model can be used for long or short term experiments, acute or chronic evaluations.

It is now proposed that as the model the rainbow trout (*Salmo gairdneri*) and the Atlantic salmon (*Salmo salar*) fry with yolk sac (alevins) be used. Experiments carried out by the inventors have shown that after hatching of trout or salmon eggs and during the yolk sac stage of the life cycle these larvae are suitable for carrying out procedures of intravital microscopy on their microcirculation. The technique of the procedures involves needle injections into the yolk sac of the fluorescent dye complex and tracer, FITC-Dx 150 (MW 150,000 daltons) and following the absorption of this material into the systemic circulation utilizing the technique of fluorescence microscopy. Using this procedure the appearance of fluorescence in ventral veins of the yolk sac absorbed from the site of injection has been documented. The only site of passage of materials in and out of the circulatory system once it has entered it, is the capillaries and the large vessels, namely, the aorta, vena cava and venous plexuses, and thus fluorescent macromolecules entering the interstitium in edema fluid can be followed and correlated with some alteration of permeability of the capillary bed (either increased or decreased permeability).

This application describes the procedure for utilizing intravital microscopy to study capillary circulation in intact, living Salmonids and other Teleost alevins (fish fry) with yolk sac attached.

As early as 1899, J. Cohnhein made microscopic observations of the vascular events in transparent tissues of both the frog, utilizing the tongue, mesentery or hindfeet of this amphibian and the fish bladder of the eel.

It is also known that in mammals, the wing of the bat, the cheekpouch of the hamster and the rat cremasteric muscle and mesentery provide suitable preparations for microscopic studies as they are thin enough to be examined in the living state with a microscope. In addition, a great deal of information in this field has come from the work done with transparent chambers inserted into the ear of the rabbit. It should be noted however that most of microcirculatory studies conducted in mammals require surgical and pharmacological interventions. Little difference, however, has been found between the results observed in amphibians, fish and in mammals.

The use of amphibian and mammalian models, for studying capillary circulation generally necessitates the preparation of paraffin or frozen sections if light microscopy is to be used or the necessity of using electron microscopy. The disadvantages of such techniques, include among others (1) the use of tissues or preparations from a sacrificed animal (2) tedious and lengthy procedures involved in preparation of sections for light and electron microscopy, involving fixation of tissues, dehydrating tissues through many alcoholic solutions, embedding in paraffin, removal of paraffin and then staining or similarly preparing tissues for electron microscopy involving fixation, mounting specimens and subsequently staining them. Because of this technology a great deal of artifact effect is produced, for example, all water and alcohol soluble materials are washed out of the specimens (3) specialized equipment as well as personnel to prepare such materials and (4) the cost of maintaining colonies of animals for study as well as the expense for providing for the care and maintenance of colonies of animals.

Fish models have been used previously to study metabolism, pharmacology, physiology, toxicology, transplantation of organs etc. Studies have been carried out in which application of fish cell cultures to biomedical research has been explored (Hightower et al. J Exp. Zoo. 1988; 248: 290–302.) A report appears in Powers. Science 1989; 4928: 352–8. on the Fish as Model Systems. Most often fish have been studied relative to environmental pollution and toxicology. Teleosts have often been used in these studies.

Some recently published articles utilizing fish for scientific studies include:

(1) The Evaluation of Hematoxic Effects of Two Commonly Used Fertilizers, Diammonium Phosphate and Urea on Fish *Clareas batrachus*. Trivedi, SP et al. Ecotoxicol Environ Safety. 1990; 2: 135–42.

(2) A Laboratory Study of The Toxicity of The Butanol Extract of Endotoxin on Two Species of Fresh Water Fish and Two Species of Aquatic Snails. Stobaeus J. K. et al. Vet Hum Toxicol. 1990; 32: 212–6.

(3) The Effect of MS22 an Anesthetic on the Peroxide Metabolic Enzymes in Erythrocytes of Fresh Water and Marine Fish Species. Gaybrelak T et al. Com Biochem Physiol. 1989; 92: 5–8.

(4) DDT Toxicity: Variation in Tissue Non-specific Phosphomonoesterases and Glucogenic Enzymes in Teleosts. Shaffi et al. Acta Physiol. 1989; 714: 57–62.

(5) Experimental Transmission of Plasma Cytoid Leukemia of Chinook Salmon. Kent et al. Cancer Res. 1990; 1:50 (17 suppl).

(6) Influence of Human Erythropoietin an l-Thyroxine on Blood Morphology and Energy Reserves in Two Tropical Species of Fed and Starved Teleosts. Pradhorn R. K. et al. Gen Comp Endocrinol. 1988; 786: 382–9.

(7) Short Term Exposure to Copper and Silver. Cyriac P. J. et al. Bull Environ Contam Toxicol. 1989; 43: 315–20.

(8) Development of Cancer of The Liver After Injection of Trout Eggs With Known Carcinogens: Zikria et al. To be published.

In accordance with the instant invention as an experimental model, the rainbow trout (*Salmo gairdneri*) and the Atlantic salmon (*Salmo salar*) fry with the yolk sac (alevins) are used in studies involving capillary circulation. Hatching of trout and salmon eggs takes 3 to 6 weeks depending on water temperature. The yolk sac stage of these fry lasts 3 to 6 weeks depending on the temperature of the water. The size of the fry is approximately 8–20 mm. Fish eggs are readily available (due to present interest in fish farming) and the hatching of eggs as well as their development to larvae (fry) can be controlled in the laboratory by manipulation of light exposure (diurnal change), and water temperature therefore they can be made available year round. The fish model requires little specialized care facilities, should be acceptable to animal activists, is inexpensive, requires no surgical or pharmacological (anesthetic) interventions and preliminary experimental results are comparable to experiments with mammals.

It has now been found that the intravital microscopic studies of capillary circulation using the instant model of injecting FITC-Dx 150 is convenient, inexpensive and practical and requires no surgical or pharmacological intervention. This model can be used for:

1) Studying inflammation, its cause, results and its modification using a readily available, inexpensive, intact, clean vertebrate.

Inflammation is the characteristic response of animals (vertebrates) to tissue injury. Whenever tissue is injured there follows at the site of injury a series of events that tend to destroy or limit the spread of the injurious agent. The early events in inflammation are mainly vascular. Agents that injure tissue include microorganisms, trauma, heat, cold, radiant and electrical energy and chemicals. Because of the diversity of the causative factors, inflammation is one of the most common and important conditions which the physician encounters. Regardless of the specific insult initiating the inflammatory response multiple substances are released by the injured tissue resulting in dramatic changes in the tissues (inflammation). Because of the demonstrated similarities of the inflammatory response to some of the effects of the immune response, the model and processes utilizing the same can be especially adapted for tracing T-cells and B cells utilizing monoclonal antibodies.

Inflammation is characterized by: (1) vasodilation of the local blood vessels; (2) increased permeability of the capillaries with leakage of fluid and proteins into the interstitial spaces; (3) clotting of the fluid in these spaces; and (4) swelling of the cells.

Tissue products released by inflammatory stimuli include histamine, bradykinin, serotonin, prostaglandins, products of the complement system, lymphokines, cell mediators etc.

(2) Toxicological studies, i.e., the studying of adverse effects of chemicals on living organisms. Toxicity tests on these fish fry can be performed to obtain information that can be used to evaluate the risk that exposure to chemicals poses to man, to study new pharmacological agents, their carcinogenic potential as well as tetralogical effects, to evaluate drug interaction and imcompatibilities, etc.

The function of the capillary is to exchange fluid, gases, nutrients, electrolytes, hormones and other substances between the blood and the interstitial space. The capillary is the only organ of the vascular system capable of performing this function. For this role, the capillary walls are very thin and are permeable to small molecular substances. Increased permeability is the end result of any factor destroying the integrity of the capillary endothelium.

A simple method of identifying and quantifying increased vascular permeability depends on the use of vital dyes. Vital dyes form complexes with plasma albumin and other plasma protein, so that their local accumulation in tissues indicate a movement of plasma protein across vascular endothelium. If no dye escapes, permeability is unaltered. It is therefore possible to measure the amount of dye that subsequently may exude into the injured tissues following some noxious stimulus. The dyes most often used in these studies are aniline dyes and specifically Evans Blue. In inflammation studies, dye has been observed to escape from the capillaries as early as 3 minutes after injury.

Circulating colloidal carbon (after IV injection) also identifies vessels having increased permeability by becoming deposited in walls of the involved vessels. Such studies usually involve electron microscopic examination of the labeled venules.

The inventors, herein, have found that FITC—Dx 150 (fluorescein isothiocyanate—dextran 150) is a particularly preferred vital dye complex for identifying and quantifying vascular permeability. There are many references to the use of FITC—dextran in cytological studies using intact animals or intact cells (Ohkuma S. Methods Enzymol. 1989; 174: 131–154). Normally FITC—Dx 150 does not pass through the capillary endothelium. The molecular weight of the dye dextran molecule is 150,000 daltons. Permeability of capillaries, for example, to myoglobulin MW 17,600, is 1:100 relative to water, to hemoglobin MW 68,000 and albumin MW 69,000, (1:10,000 relative to water). The normal permeability of the capillaries to FITC—Dx 150 is very low or negligible. (Textbook of Medical Physiology 7th ed. Arthur Guyton). In the method of the invention, the vital dye FITC—Dx 150 is injected into the yolk sac after first placing the alevin into a small thin pliable plastic bag (for immobilization). The fish fry can be pretreated with any medicant or agent, or with heat, cold, radiant or electrical energy etc. before or after the injection of the dye and then evaluated for signs of altered capillary permeability.

The intravital microscopic studies require little specialized equipment beyond that which is required for fluorescent microscopy. This includes a light source and a microscope equipped with excitation filters, reflective mirror, dark field condenser (with transmitted light) or bright field epi-illumination, objective lens, barrier filter and ocular lens. The equipment and techniques are convenient and well known to the researcher.

The epi type of illumination is used with tissue culture flasks, dishes etc, and can readily be used for the type of studies contemplated herein.

In performing studies using the model of the invention, FITC—Dx 150, 5–10% of fluorescent dextran of 150,000 daltons has been injected into the yolk sac, the model followed microscopically for the absorption of the material into the systemic circulation. Absorption of FITC—Dx 150 is accomplished within 10–30 minutes after injection. For carrying out this procedure the alevins are homed into small thin pliable plastic tubes or bags for immobilization and subsequently FITC—Dx 150 is injected using very fine glass needles constructed from small glass pipettes (micropipettes) or by using an #28G½ cc U-100 Insulin Syringe with micro-fine IV needle, into the yolk sac. The amounts of injected material can be readily calculated on the basis of the size of drops and or insulin syringes.

After injection of FITC—Dx 150, the tail of the intact fish fry, is evaluated over the desired period of time, by epi-illumination, using standard fluorescence microscopy. In accordance with the invention it has also been found that by cutting the transparent fish tail from the fish and by mounting the tail on a slide the extravasation of fluorescent molecules leaking from the capillaries can be studied using the ultraviolet fluorescent microscope.

For toxicological studies, depending on the objective of the experiment, e.g., the effects of detergents, environmental chemicals and pollutants, by-products of commercial manufacturing processes and the like, the test substance is introduced into the water vessel and the fish fry exposed for varying periods of time to the treated water. Thereafter the FITC—Dx 150 is injected into the yolk sac. For short or acute toxicity studies, if feasible (solubility factors etc.) the chemical agent and tumor cells can also be introduced into the yolk sac. This injection can be made, before, simultaneously, or after the injection of the FITC—Dx 150.

In studying pharmacologic agents, the materials can be studied independently, or two or more drugs can be combined for incompatibilities, antagonistic or enhancing effects by injecting the agents to be tested before, with or after the injection of the FITC—Dx 150. In this instance too, the results can be followed by visualizing the removed tail or by visualizing the tissues of the intact fry.

It has been found that the tetragenic or carcinogenic effect of drugs can be studied in this fish model. Egg or fish fry larval forms can be continuously bathed in a bath containing the agent to be tested for tetragenic or carcinogenic activity or the drug could be introduced directly into the yolk sac or eggs. The fish fry or young fish are sacrificed at varying periods of time and examined to see if there is any evidence of a possible tetragenic effect of the drug.

The inventors herein have also applied this animal model to inject tumor cells (Burkitt's lymphoma) into the yolk sac and then evaluated the model for growth of these cells in the fish. Fish fry, because of the nature of their immunological system are less apt to reject such tumors and therefore may serve as a good host for these cells.

The inventors have provided a model for intravital microscopic studies of capillary circulation that is new, convenient, inexpensive and practical. This model can also serve inexpensively for pharmacological, physiological, embryological, oncological, and pathological studies. The model is ideal for studying the pathology, physiology and pharmacology of inflammation. These studies can be of a short or long term nature.

The fish eggs are readily available, inexpensive, hardy and can easily be stored before hatching or allowed to hatch at a determined time by controlling and regulating the temperature of the water or the exposure to light. The rate of development of the eggs into fish fry can also be regulated by controlling the bath temperature and exposure to light. Fish eggs and larval forms can be housed in a water bath (tank) of any size dictated by the studies and quantity of fish fry required and the bath temperature controlled by a thermoregulator.

The fish larvae are homed into small plastic tubes for ease of handling and the yolk sac injected with FITC—Dx 150, with or without drugs, with a micropipette or #28G½ cc U-100 Insulin syringe with a microfine needle.

For fluorescent microscopic studies the tail is first removed and placed between two slides or the intact animal studied. For other studies, eg. pathology, embryology, oncology or tetralogy, the tissues can be processed by standard histologic techniques as indicated.

Additional values of this model are the number of animals that can be readily utilized. Fish fry are small and inexpensive and need not be housed in expensive quarters. They are relatively clean and easy to maintain. Little equipment and instrumentation is required for maintaining the fish fry or using them as a model.

There would be minimal objections by animal rights groups to the use of fish as these animals have relatively poorly developed nervous systems and further are not equated as friendly family pets.

The following example is given as illustrative of the invention but is not to be construed as limitative thereof.

A series of experiments was carried out, using the fry with yolk sac of the Atlantic salmon and rainbow trout, for studying the "capillary leak syndrome" and the effects of macromolecules on the outcome of experimentally induced "capillary leak syndrome".

Elevated temperatures are known to cause increased permeability of the rete capillaries of the eel (Effect of Temperature Change on the Permeability of Eel Rete Capillaries. Rasio EA et al. Circulation Res. 1992; 70:272–284). Fluorescent Dextran 150K (Dx-150) was injected into the 3–6 week old fish and was found to enter their circulation within 1–12 hours. A control group of 219 fish were injected with 0.05 cc of saline alone, mortality was 40% after the fry were exposed to elevated temperatures (8 degrees raised to 25 degrees C.); heat shock. Mortality in a group of 224 fish receiving HES Pz (hydroxy starch) macromolecules prior to heat shock was reduced to 26%.

A group of 17 seven week old salmon were injected with 0.05 cc FITC- Dx- 150 plus saline (50/50 solution) and the mortality was found to be 20%. Another group of 25 fish were injected with FITC Dx- 150 plus HES (hydroxy starch) molecular weight 300K-1 million daltons. The mortality rate was reduced from 20% to 6%. Intravital microscopy was carried out in both groups to ensure intravascular entry of the tracer FITC- DX-150. After the mortality determinations had been completed, the transparent tails were mounted on slides and subjected to digital image processing and integrated optical intensity measurements for fluorescent leakage. The control value was 57.39±1.85 compared to the experimental group value of 48.13±0.74 (Mann-Whitney, two tailed p=0.0002), indicating the significant sealing property of HES macromolecules. The results would appear to indicate that such macromolecules may find clinical applications in "capillary leak syndromes" such as ARDS.

While the invention has been described with reference to Salmonids and other Teleost alevins (fish fry) with yolk sac attached, it is equally applicable to amphibian species larval forms such as tadpoles with yolk sac still attached.

We claim:

1. A method for evaluating the effect of trauma attributable to exposure to one of heat, cold, radiant energy, electrical energy, toxic chemicals, carcinogens, or injected tumor cells on the capillary circulation of an intact living salmonid, other teleost alevin (fish fry) or newly hatched amphibian tadpole, each with yolk sac attached, which comprises injecting into the yolk sac a fluorescent dye complex and tracer FITC-DX (MW 150,000 daltons), following the absorption of the injected material into the systemic circulation of said living salmonid, other teleost or amphibian tadpole exposing said salmonid, other teleost or amphibian to said trauma and thereafter examining the capillary circulation of said salmonid, other teleost or amphibian utilizing fluorescence microscopy for signs of altered capillary circulation attributable to said trauma.

2. A method according to claim 1 wherein said salmonid is the rainbow trout (*Salmo gairdneri*) or the Atlantic salmon (*Salmon salar*).

3. A method according to claim 1 wherein said trauma is heat or cold induced.

4. A method according to claim 1 wherein said trauma is induced by exposure to radiant or electrical energy.

5. A method according to claim 1 wherein said trauma is induced by exposure to toxic chemicals.

6. A method according to claim 1 wherein said trauma is induced by injection of cancer cells.

7. A method according to claim 1 comprising the step of administering to said salmonid, other teleost or amphibian an anti-inflammatory agent by injection following the injection of said fluorescent dye complex, but prior to exposure to said trauma.

8. A method according to claim 1 comprising the step of administering to said salmonid, other teleost or amphibian HES PZ (hydroxy ethyl starch) by injection following the injection of said fluorescent dye complex but prior to exposure to said trauma.

9. A method according to claim 1 wherein said living salmonid, other teleost or amphibian is placed in a plastic bag just large enough to contain said living salmonid, other teleost or amphibian tadpole and sufficient water to maintain the same alive and wherein said bag is made of a plastic material permitting the insertion of a needle for carrying out said injection.

10. A method according to claim 1 wherein said living salmonid, other teleost or amphibian is placed in a glass or plastic tube just large enough to contain said living salmonid, other teleost or amphibian tadpole and sufficient water to maintain the same alive and wherein said tube is provided with means adapted for insertion into said tube of a needle for carrying out said injection.

11. A method according to claim 1 wherein the capillary circulation of the tail portion of said intact salmonid, other teleost or amphibian is examined utilizing fluorescence microscopy.

12. A method according to claim 1 wherein said tail portion is examined for extravasation of fluorescent molecules leaking out from said capillary circulation.

13. A method for evaluating potential anti-inflammatory drugs which comprises injecting into the yolk sac of an intact living salmonid, other teleost alevin (fish fry) or newly hatched amphibian, each with yolk sac attached, a fluorescent dye complex and tracer FITC-DX (MW 150,000 daltons), following the absorption of the injected material into the systemic circulation of said living salmonid, other teleost or amphibian tadpole, exposing said salmonid other teleost or amphibian to an inflammation inducing trauma, thereafter introducing a drug believed to possess anti-inflammatory activity, and thereafter examining the capillary circulation of said salmonid, other teleost or amphibian utilizing fluorescence microscopy for signs of altered capillary circulation.

14. A method for evaluating potential anti-inflammatory drugs which comprises injecting into the yolk sac of an intact living salmonid, other teleost alevin (fish fry) or newly hatched amphibian, each with yolk sac attached, a fluorescent dye complex and tracer FITC-DX (MW 150,000 daltons) following the absorption of the injected material in the systemic circulation of said living salmonid, other teleost or amphibian tadpole, introducing a drug believed to possess anti-inflammatory activity, exposing said salmonid, other teleost or amphibian to an inflammation inducing trauma, and thereafter examining the capillary circulation of said salmonid, other teleost or amphibian utilizing fluorescence microscopy for signs of altered capillary circulation.

* * * * *